United States Patent [19]

Roeder

[11] 4,336,804
[45] Jun. 29, 1982

[54] SANITARY NAPKIN WITH GARMENT SUSPENSION ADHESIVE BUT WITHOUT RELEASE PAPER COVERING

[75] Inventor: Robert J. Roeder, Appleton, Wis.

[73] Assignee: Kimberly-Clark Corporation, Neenah, Wis.

[21] Appl. No.: 246,630

[22] Filed: Mar. 23, 1981

[51] Int. Cl.³ .............................................. A61F 13/16
[52] U.S. Cl. ........................ 128/290 R; 128/DIG. 30
[58] Field of Search .......... 128/284, 286, 287, 290 R, 128/DIG. 30

[56] References Cited

U.S. PATENT DOCUMENTS

| | | | |
|---|---|---|---|
| 3,672,371 | 6/1972 | Roeder | 128/DIG. 30 |
| 4,023,570 | 5/1977 | Chinai et al. | 128/DIG. 30 |
| 4,063,559 | 12/1977 | Tritsch | 128/DIG. 30 |
| 4,195,634 | 4/1980 | DiSalvo et al. | 128/DIG. 30 |

*Primary Examiner*—C. Fred Rosenbaum
*Attorney, Agent, or Firm*—Howard Olevsky; William D. Herrick

[57] ABSTRACT

A sanitary napkin is provided in which the pressure sensitive adhesive means utilized for attachment of the napkin is covered by a pattern of nonpressure sensitive adhesive which is selectively positioned over the pattern of the pressure sensitive adhesive located on the garment facing side of a sanitary napkin.

5 Claims, 1 Drawing Figure

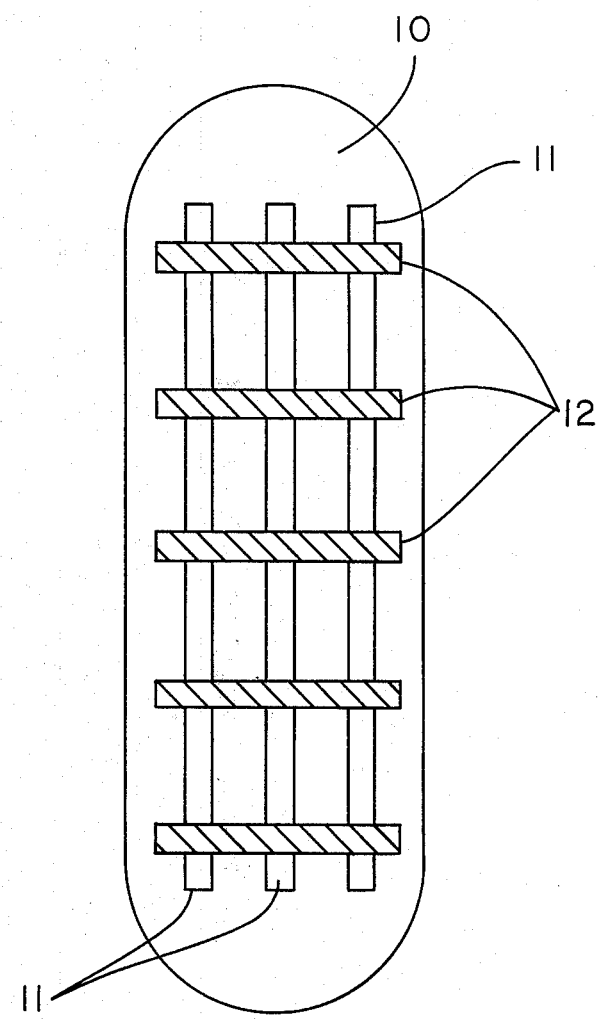

SANITARY NAPKIN WITH GARMENT SUSPENSION ADHESIVE BUT WITHOUT RELEASE PAPER COVERING

FIELD OF THE INVENTION

The subject invention relates to a sanitary napkin and particularly to a sanitary napkin having a garment suspension adhesive attached thereto.

BACKGROUND OF THE INVENTION

The so-called tabless napkins have become increasingly popular over the past several years. These napkins rather than having extended areas at either end for attachment by means of a belt have an adhesive pattern on the garment facing side thereof for direct attachment to the garment. Napkins may have this adhesive applied directly to a fluid impervious baffle or to a fluid permeable outer wrap which is overwrapped in the adhesive area. In any event, however, adhesives utilized for attachment to undergarments have been of the pressure sensitive variety and are traditionally covered with a release liner. This release liner is usually a silicone treated release paper and is maintained with low adhesive force on the pressure sensitive adhesive until the napkin is ready for use. The release liner is peeled away and the napkin is then pressed into place activating the pressure sensitive adhesive by the force utilized in producing the contact with the undergarment.

There have been problems associated with the utilization of release liners, however. For example, a separate manufacturing step is necessary to attach the release liners. Furthermore, the properties of the adhesive must be matched to that of the release surface to provide sufficient adhesion for release liner attachment without providing a strong adhesive bond requiring substantial force to separate the release liner. Improper coating of the release liner can bring about a direct paper to adhesive bond which produces nonadhesive areas on the adhesive strip when release is attempted and, in extreme cases, can render the napkin unusable due to the defect in the attachment system.

In the past, there have been attempts to eliminate the release liner from sanitary napkins. These attempts have, however, met with indifferent success. German Pat. No. 2,644,032 teaches a self-adhesive napkin in which the adhesive is insulated from contact by a perforated polyurethane foam. When the napkin is attached the foam is compressed, making small selected areas of adhesive available.

U.S. Pat. No. 4,067,337 discloses a diaper tape which needs no protective release sheet because of the utilization of an open plastic netting which prevents direct contact with the pressure sensitive adhesive. While the problems inherent in this attachment means are substantially different than those utilized with a sanitary napkin, the broad approach to the solution is somewhat similar to that taught in the German Patent referred to above. U.S. Pat. Nos. 4,010,753 and 3,853,129 show structures similar to those disclosed in U.S. Pat. No. 4,067,377.

It is apparent that both the feminine napkin art and the art associated with diapers relies upon the introduction of a covering layer in which the adhesive is made available by expressing the adhesive surface through the covering. The subject invention provides an alternative approach for eliminating release liners while providing a sanitary napkin which can be rapidly made on essentially conventional equipment.

SUMMARY OF THE INVENTION

This invention provides a sanitary napkin in which the adhesive attachment means located on the garment facing side of the adhesive are shielded by patterns of nonpressure sensitive adhesive which covers selective spaced portions of the pressure sensitive adhesive layer. The covering adhesive has a thickness of from about two to fifteen times that of the pressure sensitive adhesive layer. (The pressure sensitive adhesive layer is between 2 and 6 mils thick.) These nonpressure sensitive adhesives which are traditionally so-called hot melt adhesives are adhesive when they are applied in the hot state but lose their adhesive properties when at room temperature. After the pressure sensitive adhesive used as the garment suspension adhesive is applied, a hot melt adhesive, which is not pressure sensitive, is applied in a contrasting pattern to overlay parts of the pressure sensitive adhesive, thereby providing a substantially nontacky barrier between the pressure sensitive adhesive applied initially. The application of the hot melt adhesives is therefore, selectively shielded from a surface which might otherwise adhere to it e.g. another napkin or the ends of a package until the sanitary napkin is to be used. The curvature of the sanitary napkin as it is placed in position against an undergarment exposes the pressure sensitive adhesive for the first time to the undergarment and maintains the desired attachment. The nonpressure sensitive hot melt adhesive provides a minimal barrier to attachment due to the configuration of the napkin resulting from its positioning. The hot melt adhesive which may be polyvinyl pyrollidone for example, is currently preferred to be applied in a separate extrusion step. Both adhesives can be applied by conventionally available equipment and if the pressure sensitive adhesive is also a hot melt adhesive such as that disclosed, for example, in U.S. Pat. No. 4,136,699 issued to the H. B. Fuller Company, the adhesives both can be applied by extrusion.

DESCRIPTION OF THE DRAWINGS

The invention can best be understood by reference to the drawing which is a bottom plan view of the preferred embodiment of the napkin of this invention.

As can be seen, the garment facing side 10 which may be either a fluid impermeable baffle or an overwrap has three longitudinally extending pressure sensitive adhesive strips 11 terminating near the ends of the garment facing surface masked at selectively essentially equidistantly spaced intervals by nonpressure sensitive hot melt adhesive lines 12.

DETAILED DESCRIPTION OF THE INVENTION

Where a currently preferred pressure sensitive adhesive pattern consisting of three spaced longitudinal lines is employed, the covering nonpressure sensitive adhesive preferably crosses the pressure sensitive adhesive at five places essentially equally spaced from each other. One of these lines is positioned to essentially bisect the pressure sensitive adhesive lines and two other lines are located near each end of the adhesive. The other two lines are positioned between the center lines and those near either end.

It is apparent that the covering nonpressure sensitive adhesive need be neither straight, nor linear nor even continuous but should only cover the attachment adhesive at selectively spaced, preferably essentially equidistant portions along its length. Other pressure sensitive adhesive configurations could require different covering nonpressure sensitive adhesive patterns but it has been found that as long as 50–85% of the pressure sensitive adhesive area is exposed and selectively spaced areas are masked, adequate shielding will occur without unduly inhibiting the garment adhesive attachment qualities of the napkin.

Thickness of the covering adhesive is related to surface area covered, i.e. the larger the area covered the less thick the covering adhesive has to be. In the preferred configuration of attachment adhesive intermediate thickness levels of four to six times the thickness of the attachment adhesive can be used where about 25–35% of the surface is covered.

What is claimed is:

1. A sanitary napkin with a body facing surface and a garment facing surface, comprising in combination an absorbent batt, a fluid impermeable baffle positioned between the batt and the garment of the wearer and adhesive attachment means on the garment facing side said attachment means including a plurality of discrete portions of pressure sensitive adhesive terminating prior to the ends of the garment facing surface said pressure sensitive adhesive being covered in spaced selected areas by a nonpressure sensitive adhesive.

2. The sanitary napkin according to claim 1 wherein the pressure sensitive adhesive is from 50 to 85% uncovered.

3. The sanitary napkin according to claim 1 or 2 in which the pressure sensitive adhesive is disposed in a plurality of essentially longitudinal strips and coverage by the nonpressure sensitive adhesive is in five separate areas one of said covering areas essentially bisecting each pressure sensitive adhesive line and two other areas located near each end of each of said pressure sensitive adhesive lines.

4. The sanitary napkin according to claim 1 or 2 in which the covering adhesive is from two to fifteen times thicker than the pressure sensitive adhesive.

5. The napkin according to claim 1 wherein covering of the pressure sensitive adhesive by the nonpressure sensitive adhesive is essentially equidistant.

* * * * *